(12) United States Patent
Shizuka

(10) Patent No.: US 8,162,939 B2
(45) Date of Patent: Apr. 24, 2012

(54) MEDICAL TREATMENT DEVICE

(75) Inventor: Toshihiro Shizuka, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 1062 days.

(21) Appl. No.: 11/918,146

(22) PCT Filed: Mar. 7, 2006

(86) PCT No.: PCT/JP2006/304386
§ 371 (c)(1),
(2), (4) Date: Oct. 10, 2007

(87) PCT Pub. No.: WO2006/109377
PCT Pub. Date: Oct. 19, 2006

(65) Prior Publication Data
US 2009/0054773 A1      Feb. 26, 2009

(30) Foreign Application Priority Data

Apr. 11, 2005   (JP) ................. 2005-113925

(51) Int. Cl.
*A61B 18/14* (2006.01)
(52) U.S. Cl. .................. 606/48; 606/46
(58) Field of Classification Search .......... 606/22, 606/41, 46–50
See application file for complete search history.

(56) References Cited

U.S. PATENT DOCUMENTS

| | | | |
|---|---|---|---|
| 4,401,124 A | 8/1983 | Guess et al. | |
| 4,582,061 A | 4/1986 | Fry | |
| 4,869,259 A | 9/1989 | Elkins | |
| 5,201,314 A | 4/1993 | Bosley et al. | |
| 5,827,276 A * | 10/1998 | LeVeen et al. | 606/41 |
| 5,921,933 A | 7/1999 | Sarkis et al. | |
| 6,071,280 A * | 6/2000 | Edwards et al. | 606/41 |
| 6,238,336 B1 | 5/2001 | Ouchi | |
| 6,506,156 B1 | 1/2003 | Jones et al. | |
| 6,932,814 B2 * | 8/2005 | Wood | 606/41 |
| 2003/0208197 A1 | 11/2003 | Wood | |
| 2004/0102804 A1 | 5/2004 | Chin | |

FOREIGN PATENT DOCUMENTS

| | | |
|---|---|---|
| JP | 2000-139944 | 5/2000 |
| JP | 2001-037776 | 2/2001 |
| JP | 2001-120558 | 5/2001 |
| JP | 2003-190179 | 7/2003 |
| JP | 2005-529702 | 10/2005 |
| WO | WO 2004/000149 A1 | 12/2003 |

OTHER PUBLICATIONS

European Official Action dated Jan. 11, 2011.
European Search Report mailed Nov. 17, 2011 in corresponding European Patent Application No. 11005947.4.

* cited by examiner

*Primary Examiner* — Michael Peffley
*Assistant Examiner* — Khadijeh Vahdat
(74) *Attorney, Agent, or Firm* — Scully, Scott, Murphy & Presser, P.C.

(57) ABSTRACT

A medical treatment device inserted into a treatment instrument insertion channel of an ultrasonic endoscope inserted into a body cavity for treating an organ in the body cavity comprises a treatment probe having an electrode portion inserted and stuck into the organ in the body cavity through the treatment instrument insertion channel of the ultrasonic endoscope for radio-frequency cautery treatment of a tissue in the organ and an ultrasonic reflection portion formed on the surface of the electrode portion of the treatment probe for reflecting an ultrasonic signal from the ultrasonic endoscope.

3 Claims, 14 Drawing Sheets

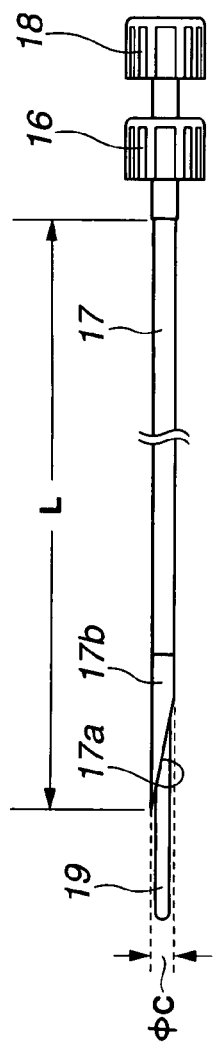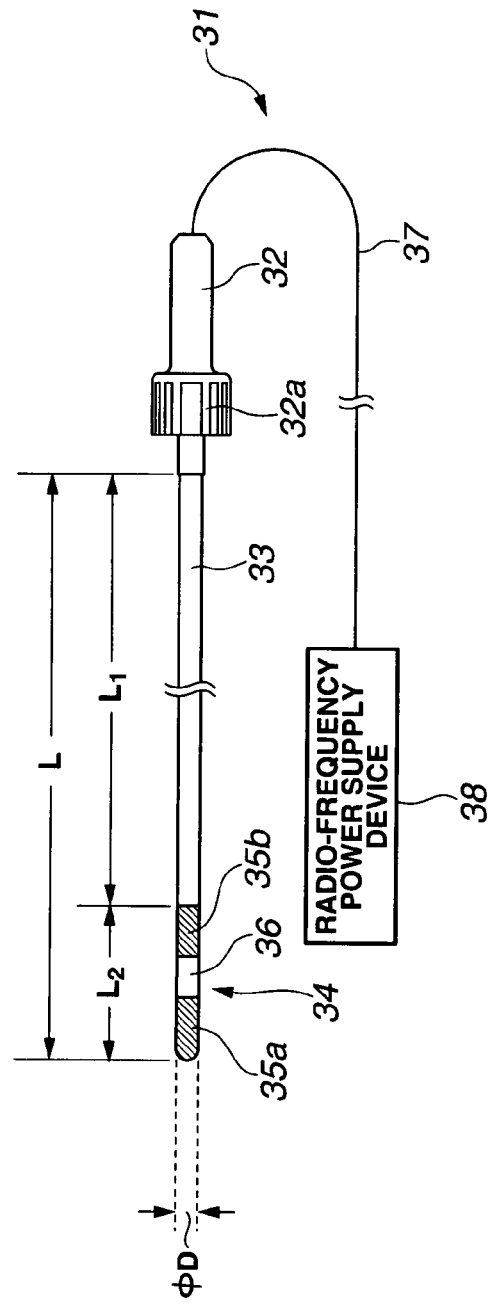

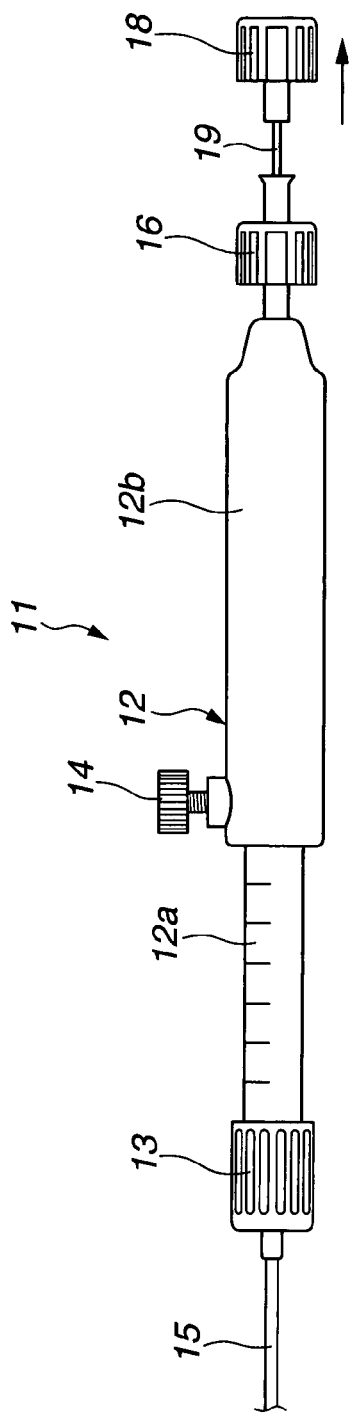
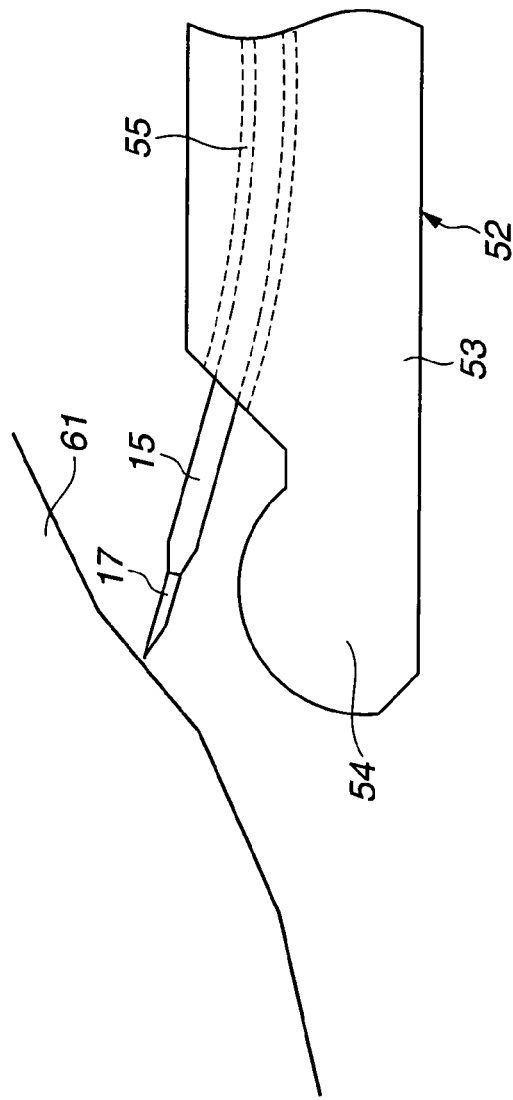

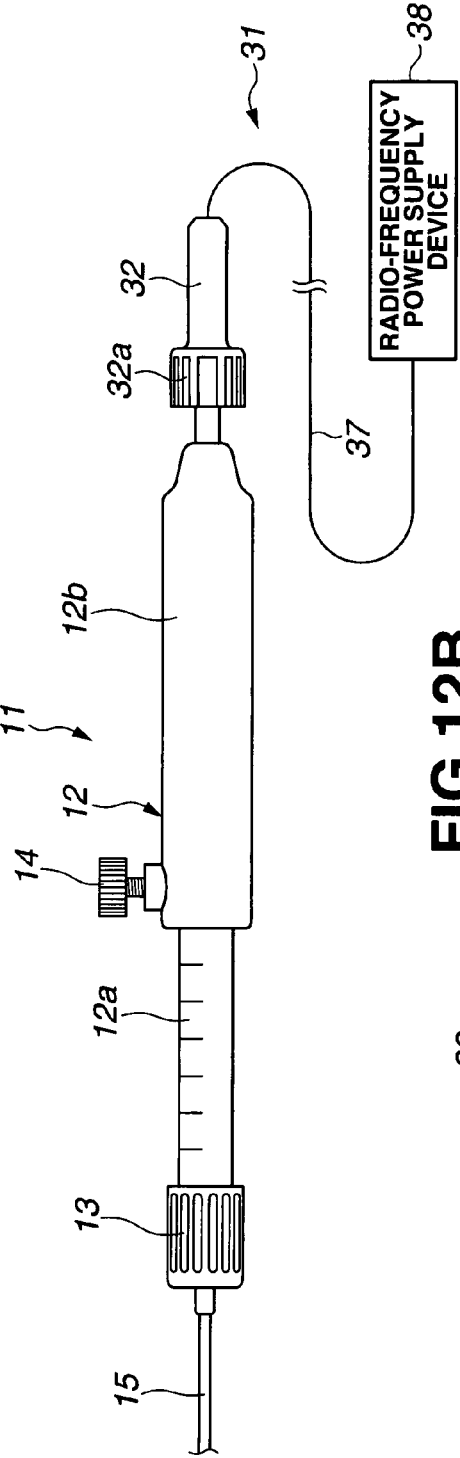
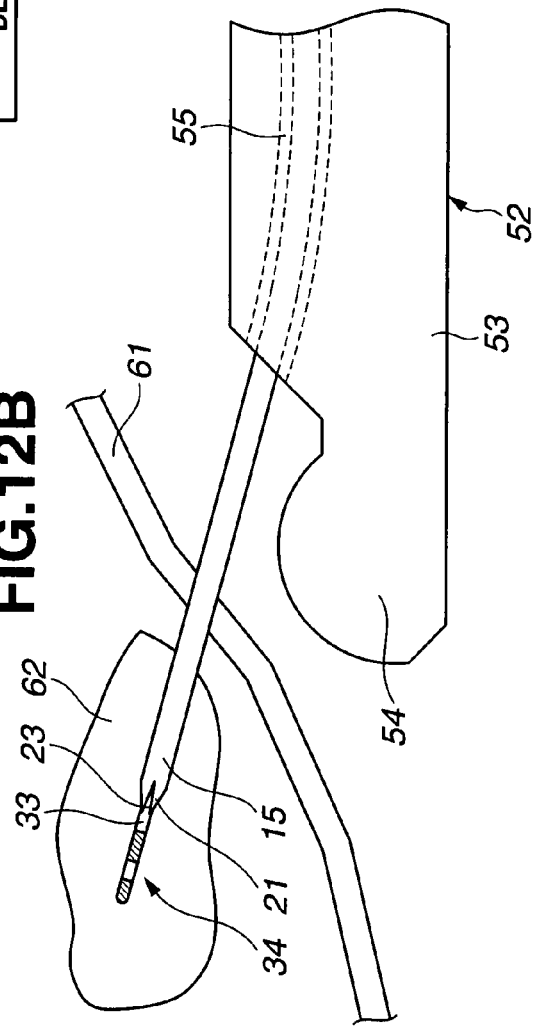

MEDICAL TREATMENT DEVICE

This application claims priority to Japanese Patent Application No. 2005-113925, filed Apr. 11, 2005, the contents of which is incorporated herein by reference.

TECHNICAL FIELD

The present invention relates to a medical treatment device which is inserted into a treatment instrument insertion channel provided to an insertion portion of an ultrasonic endoscope inserted into a body cavity for cautery treatment of an affected portion in the body cavity with a radiofrequency.

BACKGROUND ART

Recently, therapeutic treatments become possible by an ultrasonic endoscope not only for a digestive tract wall but also for a lesion in a pancreas or hepar, which is a substantial organ located deeper than the digestive tract wall. When an organ located deeper than the digestive tract wall is to be given therapeutic treatment, various medical technologies are used.

The medical technologies include a radio-frequency cautery treatment including a high-frequency cautery treatment, ablation technology such as cryotherapy, radiotherapy in which a radioactive isotope is embedded in a body, radiotherapy for treatment by radiation from outside the body and the like. In the radiotherapy in which radiation is applied from outside the body, a metal piece is indwelled in the body as a mark for positioning a lesion in an X-ray image.

In these medical technologies, a radio-frequency cautery treatment instrument or a marking member for radioactive treatment is used as a medical device. When such a medical device is guided into an organ to be treated, a puncture needle is used as the simplest way. In this case, first, a hollow puncture needle is stuck into a target portion of the organ. Next, a medical device is inserted into a through hole of the puncture needle and guided to a distal end of the puncture needle. However, it is extremely difficult to form a medical device with a small diameter so that the device can be inserted into the through hole with a small diameter of the puncture needle. If the puncture needle is made with a large diameter in order to facilitate insertion of the medical device, nonconformities such as lowered inserting capability of the puncture needle into a treatment instrument insertion channel, damage of the treatment instrument insertion channel by the puncture needle with a large diameter or deteriorated puncturing performance into an organ are worried about.

In Japanese Unexamined Patent Application Publication No. 2000-139944, for example, a radio-frequency cautery treatment instrument having excellent insertion maneuverability without damage on the treatment instrument insertion channel and smaller invasion into a patient is proposed. This radio-frequency cautery treatment instrument comprises a sheath portion to be inserted into a body cavity, a needle-state main body inserted into the sheath portion, projecting to the front from the distal end of the sheath portion, and capable of puncture into a living tissue portion, a first electrode arranged in the vicinity of the distal end portion of the sheath portion, and a second electrode provided at the distal end of the needle-state main body and separated from the first electrode. In the radio-frequency cautery treatment instrument, a bipolar electrode comprises the first electrode in the vicinity of the sheath portion distal end and the second electrode at the distal end of the needle-state main body. In a treatment using the radio-frequency cautery treatment instrument, the first electrode of the sheath portion is brought into contact with the surface of a lesion and the second electrode of the needle-state main body is stuck into the lesion. After that, the lesion is cauterized by having a radio-frequency current flown between the electrodes.

On the other hand, in Japanese Unexamined Patent Application Publication No. 2001-120558, a marking device for endoscope for detaining a marking member at a target portion in a body cavity is proposed. This marking device for endoscope comprises a hollow and lengthy catheter, a tapered needle-state puncture portion formed at the distal end of the catheter, a marking member accommodated capable of being pushed out of the puncture portion of the catheter and detained in a living tissue, a hollow pusher slidably inserted into the catheter and pushing-out and operating the marking member from the puncture portion toward the outside of the catheter, and a guide needle slidably provided in the hollow body of the pusher. At the puncture portion of the catheter, a slit is provided so that the catheter can be elastically deformed easily when the marking member is pushed out. The puncture portion of the catheter is stuck into a living tissue and the marking member accommodated in the catheter is pushed out by the pusher while being guided by the guide needle. By this operation, the marking member accommodated in the puncture portion of the catheter is detained at the target portion of the living tissue.

However, in the radio-frequency cautery treatment instrument proposed in the above Japanese Unexamined Patent Application Publication No. 2000-139944, the first electrode of the sheath portion is brought into contact with the gastric wall surface and the second electrode of the needle-state main body is stuck into the lesion close to the gastric wall from the gastric wall so as to carry out the radio-frequency cautery, for example. In this case, the radio-frequency cautery treatment is effective for the lesion in the vicinity of the gastric wall but not suitable for the cautery treatment for a lesion of an organ located at the depth of the gastric wall. That is because when the second electrode of the needle-state main body is stuck into the vicinity of the lesion of an organ located at the depth of the gastric wall for the radio-frequency cautery, a radio-frequency current is applied between the first electrode of the gastric wall surface and the second electrode stuck into the vicinity of the lesion so as to carry out the radio-frequency cautery also for the living tissue other than the lesion located between the first electrode and the second electrode.

That is, the radio-frequency cautery treatment instrument is suitable for the cautery treatment for a lesion in the vicinity of a digestive tract wall but not suitable for the cautery treatment for a lesion of an organ located deeper than the digestive tract wall.

On the other hand, the marking device for endoscope in Japanese Unexamined Patent Application Publication No. 2001-120558 is to detain the marking member at a target portion of a living tissue. Therefore, there is no suggestion at all that the radio-frequency cautery treatment instrument is inserted into a lesion of an organ located deeper than a digestive tract wall.

The present invention was made in view of the above circumstances and has an object to provide a medical treatment device capable of puncture a lesion of an organ at the depth of a body cavity so as to enable the radio-frequency cautery treatment only for the lesion.

DISCLOSURE OF INVENTION

Means for Solving the Problem

A medical treatment device to be inserted through a treatment instrument insertion channel of an ultrasonic endoscope inserted into a body cavity for treating an organ in a body cavity of the present invention comprises a treatment probe having an electrode portion to be inserted and stuck into the organ in the body cavity through the treatment instrument insertion channel of the ultrasonic endoscope for radio-frequency cautery treatment of a tissue of the organ and an ultrasonic reflection portion formed on the surface of the electrode portion of the treatment probe for reflecting an ultrasonic signal from the ultrasonic endoscope.

BRIEF DESCRIPTION OF THE DRAWINGS

FIG. 4A is a view for explaining the needle pipe and the stylet.

FIG. 4B is a view for explaining configuration of a radio-frequency treatment instrument, which is a treatment probe.

FIG. 9A is a view for explaining an operation to pull down the stylet protruding from the distal-end needle portion of the needle pipe.

FIG. 9B is a view illustrating a state where the distal-end needle portion of the needle pipe is opposed to the digestive tract wall.

FIG. 12A is a view illustrating a configuration of the handle side of the medical treatment device whose treatment probe is inserted into the guide tube.

FIG. 12B is a view illustrating a state where an electrode portion of the treatment probe is inserted and stuck into the lesion.

BEST MODE FOR CARRYING OUT THE INVENTION

An embodiment of the present invention will be described below in detail by referring to the attached drawings.

Figure 14:
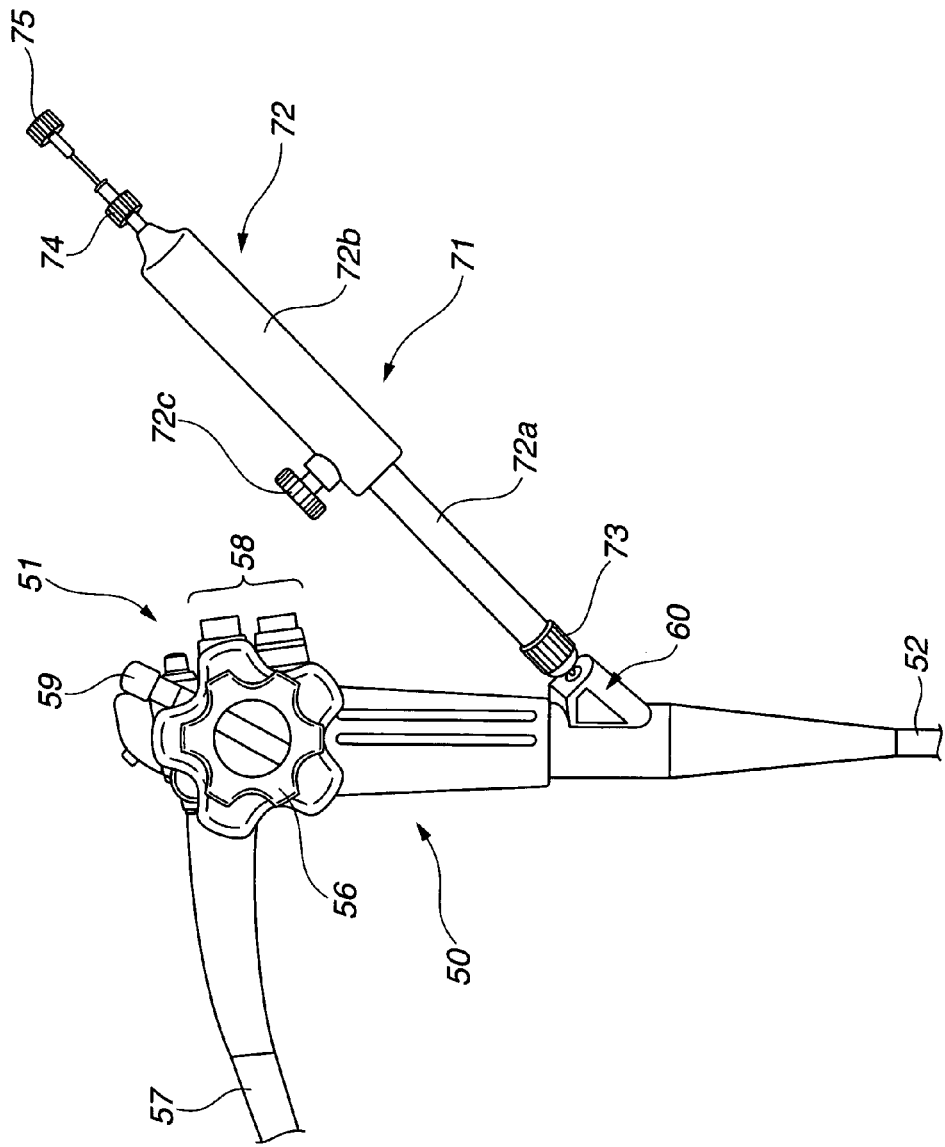
FIG. 14 is a view for explaining a relation between an ultrasonic endoscope for observing a lesion by inserting an endoscope insertion portion into a body cavity and a puncture needle, which is a treatment instrument to be inserted into a treatment instrument insertion channel provided to the endoscope insertion portion of the ultrasonic endoscope.

First, referring to FIG. 14, a relation between an ultrasonic endoscope for observing a lesion by inserting an endoscope insertion portion into a body cavity and a puncture needle, which is a treatment instrument inserted into a treatment instrument insertion channel provided at the endoscope insertion portion of the ultrasonic endoscope will be described. As shown in the figure, the ultrasonic endoscope 50 comprises an operation portion 51, an insertion portion 52, and a universal cord 57.

The insertion portion 52 is inserted into a body cavity. The insertion portion 52 comprises, though not shown, a lengthy flexible portion having flexibility provided on the side of the operation portion 51, a bending portion bent in the up and down and right and left directions, for example, and continuing to the distal end of the flexible portion, and a distal end portion continuing to the distal end of the bending portion. At the distal end portion, an observation window, an illumination window, a treatment instrument opening, an air/water feed opening, an ultrasonic transducer for transmitting/receiving an ultrasonic wave and the like, not shown, are arranged. At the treatment instrument opening, a treatment instrument raising stand is provided. Inside the flexible portion, a bending wire for bending the bending portion, an image pickup signal cable connected to an image pickup device for picking up an optical image passing trough the observation window, a light guide fiber facing the illumination window, a treatment instrument insertion tube communicating with the treatment instrument opening, a raising wire connected to the treatment instrument raising stand, an air/water feed tube communicating with the air/water feed opening, an ultrasonic signal cable connected to the ultrasonic transducer and the like are inserted.

An operation portion 51 is provided at the proximal end of the insertion portion 52. The operation portion 51 is a portion to be grasped by an operator and comprises a bending operation knob 56, an air/water feed button 58, a treatment instrument raising knob 59 and a treatment instrument insertion port 60.

The bending operation knob 56 is for bending operation of the bending portion by pulling the bending wire. The air/water feed button 58 is for feeding air/water to the air/water feed channel provided in the insertion portion 52. The treatment instrument raising knob 59 is for raising operation of the treatment instrument raising stand by pulling the raising wire. The treatment instrument insertion port 60 communicates with the treatment instrument insertion tube constituting the treatment instrument insertion channel. Into the treatment instrument insertion channel, the insertion portion of the puncture needle 71, for example, is inserted.

The universal cord 57 extends from the operation portion 51. In the universal cord 57, various signal cables, light guide fibers, air/water feed tubes and the like are inserted. At the proximal end of the universal cord 57, a connector (not shown) is provided. The universal cord 57 is connected through a connector to an ultrasonic diagnosis device provided with a signal processing circuit for generating an ultrasonic image from a driving signal for driving the ultrasonic transducer and a received echo signal, a camera control unit provided with a signal processing circuit for generating a video signal from a driving signal for driving the image pickup device and a photoelectrically converted electric signal, a light source device for supplying illumination light to a light guide, and an air/water feed pump.

At the treatment instrument insertion port 60, the puncture needle 71 is detachably attached. The puncture needle 71 comprises, for example, a handle portion 72, a handle fixing base 73, a needle pipe base 74, and a stylet base 75.

The handle portion 72 is in a substantially cylindrical shape and grasped by an operator for operation. The handle fixing base 73 is to fix the distal end of the handle portion 72 to the treatment instrument insertion port 60. The needle pipe base 74 is to fix the needle pipe inserted from the proximal end of the handle portion 72. The stylet base 75 constitutes a proximal end portion of the stylet inserted from the proximal end of the needle pipe base 74.

The handle portion 72 has a fixing portion 72a, a slide portion 72b, and a fixing screw portion 72c. The fixing portion 72a has a handle fixing base 73 at its distal end. The slide portion 72b slides along an outer circumference side of the fixing portion 72a. The fixing screw portion 72c fixes the slide portion 72b with respect to the fixing portion 72a.

On the inner circumference on the proximal end side of the slide portion 72b constituting the handle portion 72, a proximal end portion of a tube, not shown, is fixed. The tube is inserted through an inner hole of the fixing portion 72a constituting the handle portion 72 and extends toward the distal end from the handle fixing base 73. The tube is inserted through the treatment instrument insertion channel provided in the insertion portion 52 from the treatment instrument insertion port 60. The distal end of the tube inserted into the treatment instrument insertion channel from the treatment instrument insertion port 60 is protruded toward the distal end from the treatment instrument opening provided at the distal end portion of the insertion portion 52. A protruding amount of the tube from the treatment instrument opening can be adjusted by sliding the slide portion 72b of the handle portion 72. The needle pipe base 74 is provided at the proximal end of the needle pipe. The needle pipe is inserted into a through hole of the tube from the proximal end of the slide portion 72b constituting the handle portion 72. The distal end portion of the needle pipe is extended toward the distal end of the tube from the distal-end opening of the tube protruded from the treatment instrument opening. The stylet is inserted into the through hole of the needle pipe from the needle pipe base 74. The distal end portion of the stylet is protruded toward the distal end of the needle pipe from the distal-end opening of the needle pipe protruded from the treatment instrument opening.

That is, in the puncture needle 71, the tube whose proximal end is fixed to the handle portion 72 is inserted through the treatment instrument insertion channel of the insertion portion 52 of the ultrasonic endoscope 50. After that, by penetrating the needle pipe inserted through the tube to the lesion or by inserting and penetrating the radio-frequency cautery treatment instrument into the lesion instead of the needle pipe, treatment or the like can be carried out for the lesion.

The medical treatment device shown in the embodiment of the present invention is capable of observation of the lesion in a body cavity by the ultrasonic endoscope 50 and a treatment for a lesion with the treatment instrument introduced through the puncture needle 71 inserted into the treatment instrument insertion channel provided to the insertion portion 52 of the ultrasonic endoscope 50. Specifically, radio-frequency cautery treatment only for a lesion of an organ located at the depth of a body cavity is enabled.

A configuration of the medical treatment device of the present invention will be described referring to FIGS. 1 to 6.

Figure 1:
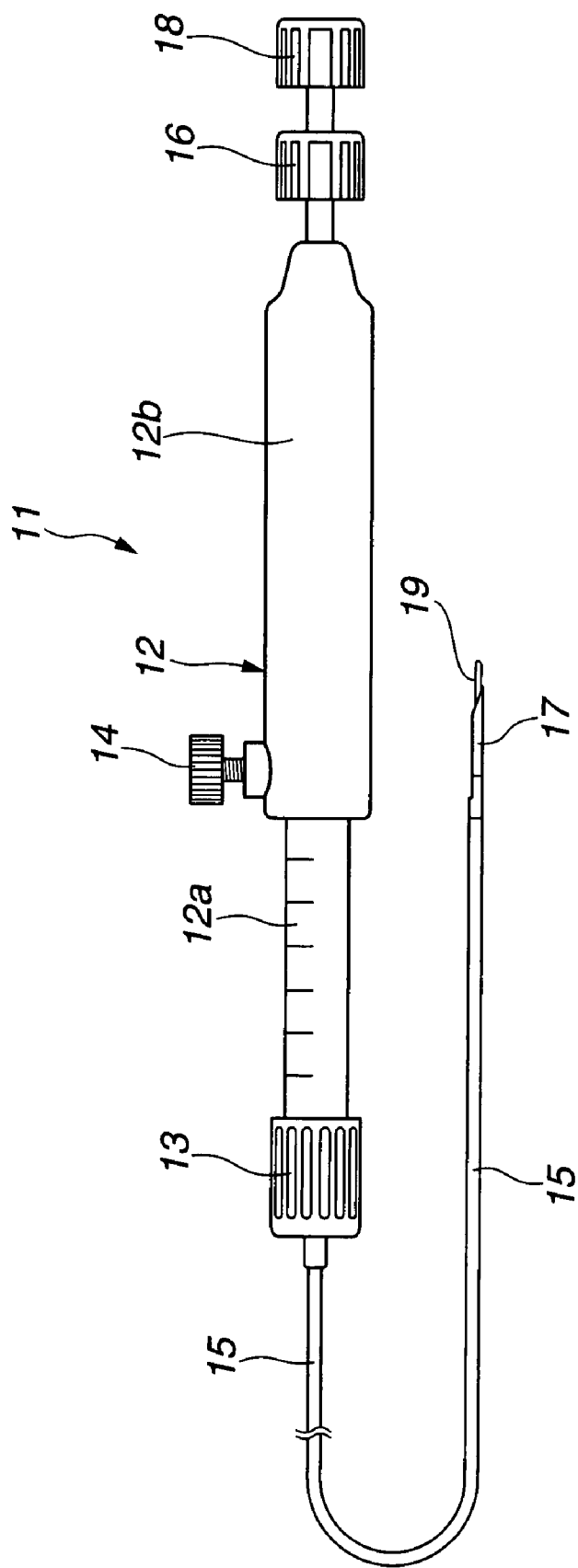
FIG. 1 is a view for explaining configuration of a medical treatment device.

FIG. 1 is a view for explaining the medical treatment device.

In a medical treatment device 11 shown in the figure, a handle 12, a handle base 13, a hollow guide tube 15, a needle pipe base 16 having a needle pipe 17, and a stylet base 18 having a stylet 19 constitute a so-called puncture needle. By combining a radio-frequency cautery treatment instrument, which is a treatment probe as will be described later, instead of the needle pipe 17, the medical treatment device 11 for carrying out the radio-frequency cautery treatment is constituted.

The handle 12 is in a substantially cylindrical shape. The handle base 13 is provided at the distal end side of the handle 12. The hollow guide tube 15 is extended toward the distal end side from the handle base 13. The guide tube 15 is fixed on the inner circumference of the proximal end of the handle 12. The needle pipe 17 is inserted into a through hole of the guide tube 15 from the proximal end opening of the handle 12. The stylet 19 is inserted into a through hole of the needle pipe 17 from the needle pipe base 16.

The handle 12 comprises a fixing portion 12a provided with the handle base 13, a slider portion 12b, and a fixing screw 14.

The fixing portion 12a is in a pipe shape. The slider portion 12b is cylindrical, and slidably inserted and attached along the outer circumferential face of the fixing portion 12a. The fixing screw 14 is provided at the slider portion 12b. The fixing screw 14 fixes the slider portion 12b with respect to the fixing portion 12a at a predetermined position.

The proximal end (not shown) of the guide tube 15 is fixed to the inner circumferential face of the proximal end side of the slider portion 12b constituting the handle 12. The guide tube 15 fixed at the proximal end of the slider portion 12b is inserted through an inner hole of the fixing portion 12a and extended toward the distal end side in the axial direction of the handle 12 from the handle base 13.

Therefore, by sliding the slider portion 12b constituting the handle 12 in the axial direction with respect to the fixing portion 12a, an extended amount of the guide tube 15 can be adjusted. That is, the extended amount of the guide tube 15 extended from the handle base 13 can be adjusted according to sliding of the slider portion 12b. By fixing the sliding position of the slider portion 12b by the fixing screw 14, the extended amount of the guide tube 15 can be fixed.

The handle base 13 fixes the handle 12 to the treatment instrument insertion port 60. When the handle base 13 is fixed to the treatment instrument insertion port 60, the guide tube 15 extended from the handle base 13 is inserted from the treatment instrument insertion port 60 provided at the operation portion 51 of the ultrasonic endoscope 50.

The needle pipe 17 is inserted into the through hole of the guide tube 15 from the proximal end of the slider portion 12b of the handle 12 and protruded toward the distal end from the distal-end opening of the guide tube 15. The needle pipe base 16 is fixed to the proximal end of the slider portion 12b of the handle 12 in order to maintain the protruding state of the needle pipe 17 protruded toward the distal end from the distal end of the guide tube 15.

The stylet 19 is inserted into the through hole of the needle pipe 17 from the needle pipe base 16 and protruded toward the distal end from the distal end of the needle pipe 17. The stylet base 18 is fixed to the needle pipe base 16 in order to maintain the state of the stylet 19 protruded toward the distal end from the distal end of the needle pipe 17.

The guide tube 15 has flexibility and can be inserted into the treatment instrument insertion channel provided to the insertion portion 52 of the endoscope 50. The needle pipe 17 is formed relatively flexible except the needle portion at the distal end. The stylet 19 is formed by a slightly hard member. The stylet 19 is inserted and arranged in the through hole of the needle pipe 17 formed flexibly. By this arrangement, the needle pipe 17 is made hard as appropriate so as to improve the insertion operability into the guide tube 15 of the needle pipe 17. The stylet 19 prevents the guide tube 15 from being damaged by the distal-end needle portion of the needle pipe 17.

Figure 2:
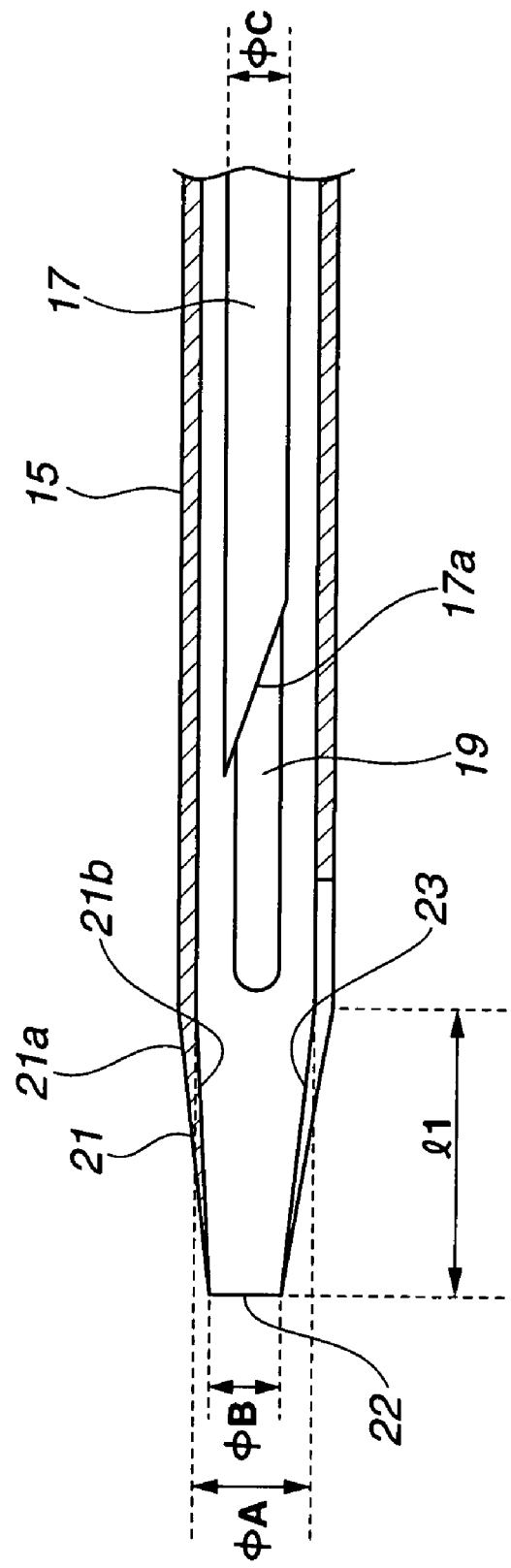
FIG. 2 is a sectional view illustrating a relation among a distal end portion of a guide tube, which is a medical treatment device, a needle pipe to be inserted through the guide tube, and a stylet to be inserted through the needle pipe.

Next, the relation among the guide tube 15, the needle pipe 17, and the stylet 19 will be described using FIG. 2.

The guide tube 15 is a guide member formed lengthy by an elastic member having flexibility. The guide tube has an insertion path 15a, which is a through hole with an inner diameter of $\phi A$. Into the insertion path 15a, the needle pipe 17 and the treatment probe are inserted. The inner diameter $\phi A$ of the insertion path 15a of the guide tube 15 is larger than an outer diameter $\phi C$ of the needle pipe 17. That is, the relation of $\phi A > \phi C$ is set. The inner diameter $\phi A$ of the insertion path 15a is an outer diameter dimension larger than the outer diameter $\phi C$ of the needle pipe 17. That is larger than an outer diameter of the treatment probe, which will be described later.

The distal end portion of the guide tube 15 is constructed as a taper portion 21 with a tapered distal end. The taper portion 21 includes an inner face 21b and an outer face 21a. The taper portion 21 sets the diameter dimension of its distal-end opening 22 at $\phi B$. The diameter dimension 4B of the distal-end opening and the outer diameter $\phi C$ of the needle pipe 17 are substantially the same, that is, they are set at $\phi B = \phi C$. In the taper portion 21, both the inner diameter and outer diameter dimensions are in the tapered shape from a position with a distance 11 (approximately several cm) from the distal-end opening 22 toward the distal end. Moreover, in the taper portion 21, a slit 23 with a predetermined length dimension is formed along the axial direction of the guide tube 15 from the side of the distal-end opening 22.

Into the insertion path 15a of the guide tube 15, the stylet 19 is inserted and the needle pipe 17 with an appropriate hardness is inserted. The distal-end needle portion 17a of the needle pipe 17 is protruded toward the distal end from the distal-end opening 22 via the taper portion 21. When the needle pipe 17 is protruded from the distal-end opening 22 of the taper portion 21, since the diameter 4B of the distal-end opening 22 and the outer diameter $\phi C$ of the needle pipe 17 are equal, the distal-end opening 22 and the outer circumferential face of the needle pipe 17 are brought into a close contact state with a slight step.

When the treatment probe having an outer diameter larger than the needle pipe 17 is inserted into the insertion path 15a of the guide tube 15, the diameter of the distal-end opening 22 is expanded by the treatment probe. This is because the slit 23 is provided at the taper portion 21. Therefore, the treatment probe can be protruded toward the distal end form the distal-end opening 22.

Figure 3A:
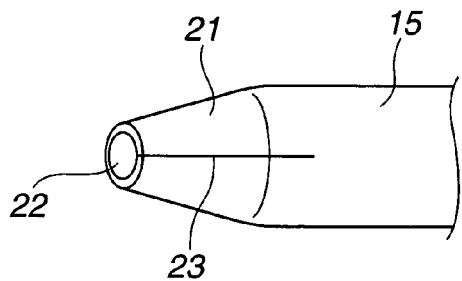
FIG. 3A is a view for explaining a configuration example of a distal-end opening and a slit provided at a taper portion.

Next, the distal-end opening 22 of the taper portion 21 and the slit 23 provided at the guide tube 15 will be described using FIGS. 3A to 3D. FIG. 3A is a view for explaining a configuration example of the distal-end opening and the slit provided at the taper portion, FIG. 3B is a view for explaining another configuration example of the distal-end opening and the slit provided at the taper portion, FIG. 3C is a sectional view cut along a cutting line 3C-3C in FIG. 3B, and FIG. 3D is a diagram for explaining a configuration example of a plurality of slits provided at the taper portion.

As shown in FIG. 3A, the distal-end opening 22 of the taper portion 21 provided at the guide tube 15 forms an opening in a direction crossing the axis of the guide tube 15. If the distal-end opening 22 is formed in a direction crossing the axis of the guide tube 15, the slit 23 is formed by one cutaway in the axial direction of the guide tube 15 from the distal-end opening 22 at the taper portion 21. When the treatment probe or the like with an outer diameter larger than the diameter 4B of the distal-end opening 22 is inserted, the taper portion 21 has the slit 23 pushed and expanded by the treatment probe with the larger outer diameter and elastically deformed. By this, the diameter 4B of the distal-end opening 22 is expanded into the diameter-expanded state. As a result, the treatment probe with the diameter dimension larger than the needle pipe 17 can be inserted into the distal-end opening 22 of the taper portion 21.

Figure 3B:
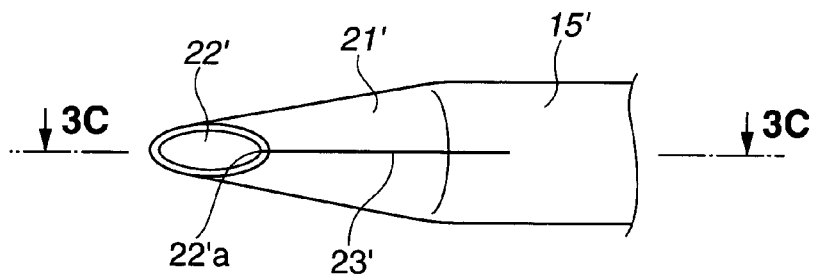
FIG. 3B is a view for explaining another configuration example of the distal-end opening and the slit provided at the taper portion.
Figure 3C:
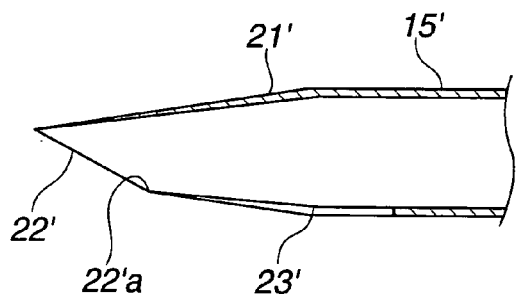
FIG. 3C is a sectional view cut away along a cutting line 3C-3C in FIG. 3B.
Figure 3D:
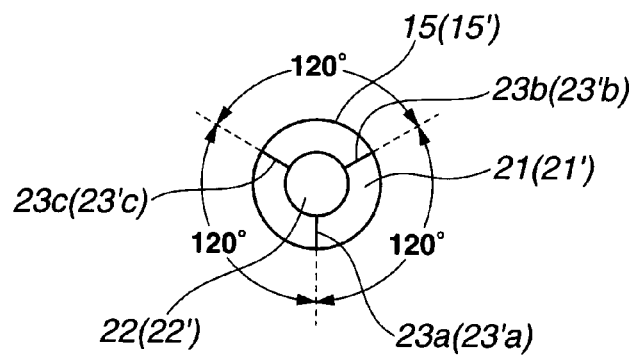
FIG. 3D is a diagram for explaining a configuration example of a plurality of slits provided at the taper portion.

As shown in FIG. 3B, a distal-end opening 22' of a taper portion 21' provided at a guide tube 15' forms an opening in a direction diagonal to the axis of the guide tube 15'.

Therefore, the distal-end opening 22' is a substantially oval opening as shown in FIG. 3B. And the substantially oval distal-end opening 22' has its long diameter and short diameter set in close contact with the outside of the needle pipe 17 to be inserted. A slit 23' is formed at the taper portion 21' by a single cut, from a proximal end side 22'a of the guide tube 15' which is a long diameter side of the distal-end opening 22' (hereinafter also described as a jaw side 22'a of the distal-end opening 22') in the axial direction of the guide tube 15'. The taper portion 21' is brought into diameter-expanded state where the distal-end opening 22' is expanded since the slit 23' is pushed wide and elastically deformed.

The guide tubes 15, 15' having the taper portions 21, 21' at the distal end portion are capable of puncture into a living tissue together with the needle pipe 17 to be stuck into the living tissue, though the detail will be described later.

When the slits 23, 23' are provided at the taper portions 21, 21', as shown in FIG. 3D, three slits 23a, 23b, 23c may be formed with an interval of approximately 120 degrees, for example. By this arrangement, the diameters of the taper portions 21, 21' can be expanded more easily. However, when the distal-end opening 22' opened diagonally to the axial direction of the guide tube 15 shown in FIGS. 3B, 3C is provided, a slit is formed with an interval of 120 degrees with the slit 23' of the jaw side 22'a as reference. That is, the position of the slit 23a in FIG. 3D is brought to the jaw side 22'a and the other two slits with the 120-degree interval are provided. That is because if the slit 23' is provided on the distal end side of the long diameter of the diagonally opened distal-end opening 22', that is, the side opposite the jaw side, there is a fear that the distal-end opening 22' of the taper portion 21' is turned up by the living tissue and that makes puncture difficult when the taper portion 21' of the guide tube 15 is guided by the needle pipe 17 and stuck into the living tissue.

Next, a radio-frequency cautery treatment instrument (hereinafter described as a treatment probe) 31, which is a treatment probe to be inserted into the insertion path 15a of the guide tube 15 will be described using FIG. 4B.

The treatment probe 31 comprises a grasping portion 32, a lengthy cylindrical flexible pipe portion 33, an electrode portion 34, and a radio-frequency power supply device 38.

The grasping portion 32 is a portion to be grasped by an operator. The flexible pipe portion 33 is formed by an insulating flexible member and the proximal end is fixed to the grasping portion 32. The electrode portion 34 is provided on the surface of the distal end of the flexible pipe portion 33. From the grasping portion 32, a signal cable 37 is extended. The signal cable is connected to the radio-frequency power supply device 38.

At the grasping portion 32, a base 32a is provided. The base 32a fixes the grasping portion 32 to the proximal end of the slider portion 12b. At that time, the flexible pipe portion 33 is inserted from the proximal end of the slider portion 12b of the handle 12 constituting the medical treatment device 11.

The flexible pipe portion 33 is provided with the electrode portion 34 constituting the bipolar electrode on the surface of its distal end portion. The electrode portion 34 is provided with a first electrode 35a, a second electrode 35b, and an insulation portion 36. The insulation portion 36 is provided between the first electrode 35a and the second electrode 35b. The first electrode 35a and the second electrode 35b are formed annularly on the surface of the outer circumference of the flexible pipe portion 33. To the first electrode 35a and the second electrode 35b, a signal cable is electrically connected, respectively. The signal cable connected to the first electrode 35a and the second electrode 35b, respectively, is inserted through the flexible pipe portion 33 and the grasping portion 32 and extended as a signal cable 37 from the proximal end of the grasping portion 32. The end of the signal cable 37 is electrically connected to the radio-frequency power supply device 38 through a connector, not shown. The radiofrequency power supply device 38 supplies a radio-frequency current, which is a frequency different in polarity, to the first electrode 35a and the second electrode 35b constituting the electrode portion 34 through the signal cable 37.

While the electrode portion 34 is inserted into the living tissue, a predetermined radio-frequency current is supplied to the electrode portion 34 from the radio-frequency power supply device 38. Then, the radio-frequency current is made to flow between the first electrode 35a and the second electrode 35b through the living tissue. Then, the living tissue energized by the radio-frequency current is cautery-treated by the energized radio-frequency current. The insulation portion 36 constituting the electrode portion 34 maintains insulation between the first electrode 35a and the second electrode 35b and an interval between the first electrode 35a and the second electrode 35b at a predetermined distance. According to the interval between the first electrode 35a and the second electrode 35b set by the insulation portion 36, a cautery range by the radio-frequency current energized between the first electrode 35a and the second electrode 35b through the living tissue is changed. Moreover, according to the interval between the first electrode 35a and the second electrode 35b, a radio-frequency current value supplied from the radio-frequency power supply device 38 to the electrode portion 34 is different. Therefore, by setting the interval between the first electrode 35a and the second electrode 35b by the insulation portion 36 so as to change the radio-frequency current to be supplied, the cautery range of the living tissue can be changed as appropriate.

The outer diameter $\phi D$ on the distal end side of the flexible pipe portion 33 having the electrode portion 34 in the treatment probe 31 is larger than the outer diameter $\phi C$ of the needle pipe 17 as mentioned above. That is, the relation of $\phi D > \phi C$ is set. However, the distal-end side outer diameter $\phi D$ of the flexible pipe portion 33 of the treatment probe 31 is formed smaller than the inner diameter $\phi A$ of the insertion path 15a of the guide tube 15, as mentioned above. That is, the relation of $\phi D < \phi A$ is set.

As shown in FIG. 4A, a length of the distal-end needle portion 17a constituting the needle pipe 17 from the distal-most end to the needle pipe base 16 is L. The length of the flexible pipe portion 33 constituting the treatment probe 31 is the length from the distal end of the electrode portion 34 to the base 32a of the grasping portion 32 as shown in FIGS. 4A and 4B and is set at the same dimension as the length L from the distal-most end of the distal-end needle portion 17a to the needle pipe base 16.

Figure 5A:
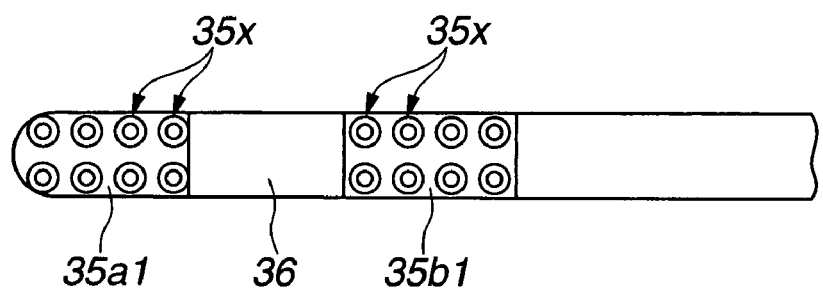
FIG. 5A is a plan view for explaining a configuration example of an ultrasonic reflective surface provided on the surface of an electrode.
Figure 5B:
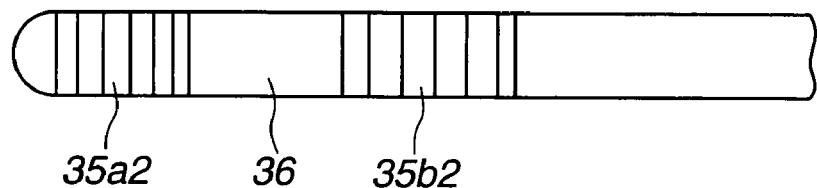
FIG. 5B is a plan view for explaining another configuration example of an ultrasonic reflective surface provided on the surface of an electrode.
Figure 5C:
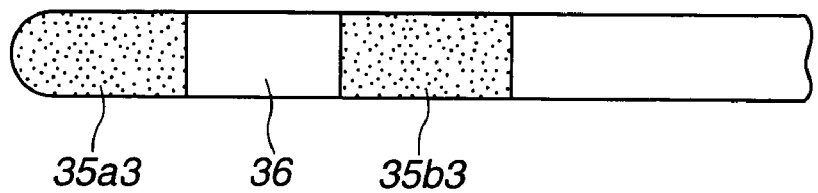
FIG. 5C is a plan view for explaining still another configuration example of an ultrasonic reflective surface provided on the surface of an electrode.
Figure 6A:
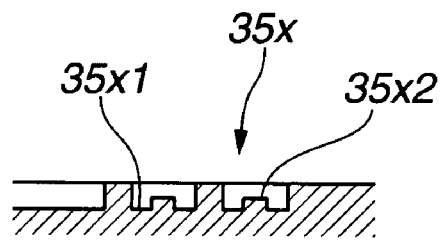
FIG. 6A is a sectional view for explaining a sucker constituting the ultrasonic reflective surface in FIG. 5A.
Figure 6B:
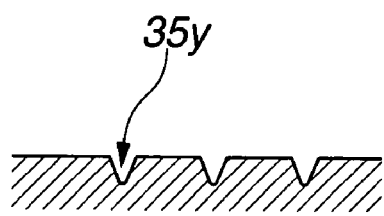
FIG. 6B is a sectional view for explaining a groove portion constituting the ultrasonic reflective surface in FIG. 5B.
Figure 6C:
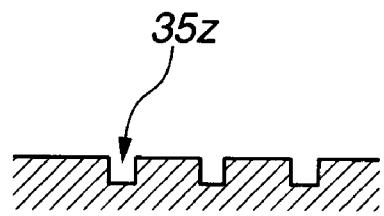
FIG. 6C is a sectional view for explaining a groove portion constituting the ultrasonic reflective surface in FIG. 5B.

The electrode surfaces of the first electrode 35a and the second electrode 35b provided to the electrode portion 34 of the treatment probe 31 will be described using FIGS. 5A to 6C. FIG. 5A is a plan view for explaining a configuration example of an ultrasonic reflective surface provided on the surface of the electrode, FIG. 5B is a plan view for explaining another configuration example of an ultrasonic reflective surface provided on the surface of an electrode, FIG. 5C is a plan view for explaining still another configuration example of an ultrasonic reflective surface provided on the surface of an electrode, FIG. 6A is a sectional view for explaining a sucker constituting the ultrasonic reflective surface in FIG. 5A, FIG. 6B is a sectional view for explaining a groove portion constituting the ultrasonic reflective surface in FIG. 5B, FIG. 6C is a sectional view for explaining a groove portion constituting the ultrasonic reflective surface in FIG. 5B.

The electrode portion 34 of the treatment probe 31 needs to be accurately inserted into a lesion, which is a treatment portion in the living tissue. Thus, the operator confirms the lesion and the position of the electrode portion 34 of the treatment probe 31 inserted into the lesion from an ultrasonic image by the ultrasonic endoscope 50. However, the first electrode 35a and the second electrode 35b constituting the electrode portion 34 provided at the distal end of the flexible pipe portion 33 of the treatment probe 31 are annular state. When the electrodes 35a, 35b are constituted annularly, an ultrasonic signal emitted from an ultrasonic transducer of the ultrasonic endoscope 50 is more reflected by the electrodes 35a, 35b in a direction different from the direction of the ultrasonic transducer. That is, a reflective ultrasonic signal, which is an echo signal returning to the ultrasonic transducer, becomes weak. Therefore, the position of the electrode portion 34 of the treatment probe 31 is displayed vaguely in the ultrasonic image.

Then, in the treatment probe 31 constituting the medical treatment device 11 of the present invention, in order to have the ultrasonic signal reflected efficiently, an ultrasonic reflective surface is provided at each of the first electrode 35a and the second electrode 35b constituting the electrode portion 34.

On the surface of a first electrode 35a1 and a second electrode 35b1 constituting the electrode portion 34 shown in FIG. 5A, a plurality of sucker-state portions 35x to be ultrasonic reflection portions forming the ultrasonic reflective surface are provided. The sucker-state portions 35x formed on the surface of the first electrode 35a1 and the second electrode 35b1 comprise, as shown in FIG. 6A, somewhat deep circular recesses 35x1 and circular projections 35x2 projected from the bottom face of the circular recesses 35x1. The circular projection 35x2 is located at the center portion of the circular recess 35x1 and formed lower than the electrode surface. Thus, by providing the plurality of sucker-state portions 35x on the surfaces of the first electrode 35a1 and the second electrode 35b1, more ultrasonic signals emitted from the ultrasonic transducer are reflected by the sucker-state portions 35x toward the ultrasonic transducer. By this, many of the reflective ultrasonic signals reflected by the ultrasonic reflective surface are made to enter the ultrasonic transducer.

Also, on the surface of a first electrode 35a2 and a second electrode 35b2 constituting the electrode portion 34 shown in FIG. 5B, a plurality of groove portions as the ultrasonic reflection portion forming the ultrasonic reflective surface are provided. The groove portion formed on the surfaces of the first electrode 35a2 and the second electrode 35b2 is a groove 35y with the V-shaped section as shown specifically in FIG. 6B or a groove 35z with the rectangular section as shown in FIG. 6C. The groove 35y with the V-shaped section or the groove 35z with the rectangular section provided on the surface of the first electrode 35a2 and the second electrode 35b2 are formed in plural with an equal interval or formed continuously in the helical state. By providing a plurality of groove portions on the surface of the first electrode 35a2 and the second electrode 35b2, more ultrasonic signals emitted from the ultrasonic transducer are reflected by the groove portions toward the ultrasonic transducer. By this, many of the reflective ultrasonic signals reflected by the ultrasonic reflective surface are made to enter the ultrasonic transducer.

Moreover, on the surfaces of a first electrode 35a3 and a second electrode 35b3 constituting the electrode portion 34 shown in FIG. 5C, a rough-surfaced portion as an ultrasonic reflection portion forming the ultrasonic reflective surface is provided. The rough-surfaced portion formed on the surface of the first electrode 35a3 and the second electrode 35b3 is a rough surface formed using an abrasive or the like so that the ultrasonic wave can be easily reflected. By providing the rough-surfaced portion on the surface of the first electrode 35a3 and the second electrode 35b3 as above, more ultrasonic signals emitted from the ultrasonic transducer are reflected by the rough-surfaced portion toward the ultrasonic transducer. By this, many of the reflective ultrasonic signals reflected by the ultrasonic reflective surface are made to enter the ultrasonic transducer.

On the other hand, a puncture position into the living tissue or the like of the needle pipe 17 is monitored by the ultrasonic image. Thus, it is preferable to form the ultrasonic reflective surface also at the distal end portion of the needle portion 17 in a range of a predetermined length dimension from the distal-most end of the distal-end needle portion 17a. Then, as shown in FIG. 4A, the needle pipe 17 with the same entire length L as the treatment probe 31, and an ultrasonic reflective surface 17b is formed at the needle pipe 17. The length and the position of the ultrasonic reflective surface 17b of the needle pipe 17 are the same as a length L2 of the electrode portion 34 of the treatment probe 31 and the position thereof. The ultrasonic reflective surface 17b formed at the distal end portion of the needle pipe 17 is the same shape as that of the ultrasonic reflective surface described in FIGS. 5A to 6C or a plurality of streak-state groove portions provided in the axial direction of the needle pipe 17 so that the needle pipe 17 can be easily stuck into the living tissue.

That is, the needle pipe 17 with the same length as the length L of the flexible pipe portion 33 of the treatment probe 31 is provided with the ultrasonic reflective surface 17b with the same position and length L2 as those of the electrode portion 34 having the ultrasonic reflective surface provided at the distal end of the flexible pipe portion 33 of the treatment probe 31. By this arrangement, when the needle pipe 17 is stuck into the lesion, the ultrasonic signal is reflected by the ultrasonic reflective surface 17b and many reflective ultrasonic signals enter the ultrasonic transducer. Then, the distal end portion of the needle pipe 17 is clearly displayed in the ultrasonic image, and the operator can easily confirm the state of puncture by the needle pipe 17 into the lesion. Also, after the needle pipe 17 is pulled out of the guide tube 15, the treatment probe 31 is re-inserted into the puncture spot of the needle pipe 17 through the guide tube 15. At that time, the operator can observe the ultrasonic image and set the position having been punctured by the needle pipe 17 and the insertion position of the treatment probe 31 substantially at the same position.

Figure 7A:
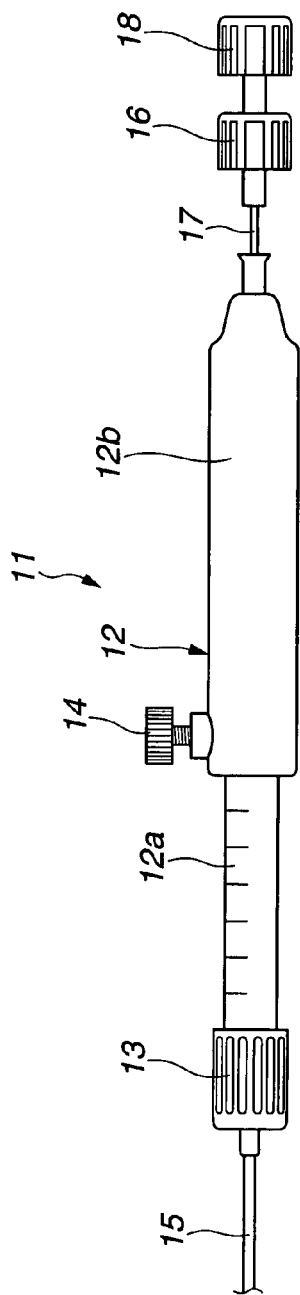
FIG. 7A is a view illustrating configuration of a handle side of the medical treatment device whose needle pipe is inserted into a guide tube.
Figure 7C:
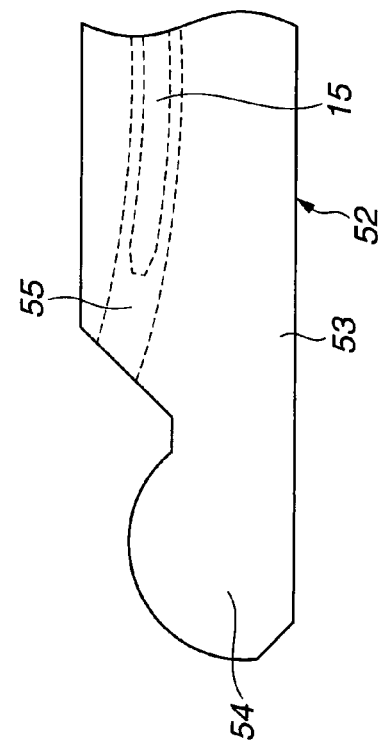
FIG. 7C is a view illustrating a state where the guide tube of the medical treatment device is inserted into the distal end of the treatment instrument insertion channel.
Figure 7B:
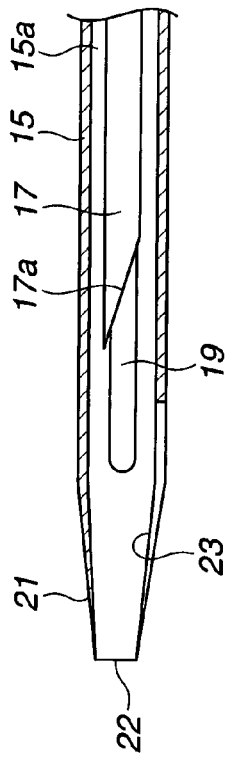
FIG. 7B is a view illustrating a state of the guide tube distal end side of the medical treatment device.

Next, action of the above-mentioned medical treatment device 11 under the observation of the lesion in the body cavity by the ultrasonic endoscope 50 will be described referring to FIGS. 7A to 12B. FIG. 7A is a view illustrating a configuration of a handle side of the medical treatment device whose needle pipe is inserted into a guide tube, FIG. 7B is a view illustrating a state of the guide tube distal end side of the medical treatment device, and FIG. 7C is a view illustrating a state where the guide tube is inserted into the distal end of the treatment instrument insertion channel of the medical treatment device.

In the medical treatment device 11 of the present invention, the guide tube 15 is inserted into the treatment instrument insertion channel from the treatment instrument insertion port 60 provided at the operation portion 51 of the ultrasonic endoscope 50. The medical treatment device 11 comprises, as shown in FIG. 7A, by inserting the needle pipe 17 into which the stylet 19 is inserted from the proximal end of the handle 12 into the guide tube 15. The relation between the needle pipe 17 inserted into the guide tube 15 and the stylet 19 is, as shown in FIG. 7B, a state where the distal end portion of the stylet 19 is protruded from the distal-end needle portion 17a of the needle pipe 17. The needle pipe 17 is relatively flexible, and if only the needle pipe 17 is inserted into the guide tube 15, the insertion force applied to the needle pipe base 16 is not fully transmitted to the distal end of the needle pipe 17 and the insertion operability is lowered. Also, the distal-end needle portion 17a of the needle pipe 17 is sharp and might damage the guide tube 15. Therefore, the stylet 19 formed by a member harder than the needle pipe 17 is inserted into the needle pipe 17 so as to somewhat harden the entire needle pipe 17. By this, the insertion performance when the needle pipe 17 is inserted into the guide tube 15 is improved. In addition, by protruding the distal end portion of the stylet 19 toward the distal end from the distal-end needle portion 17a, damage on the guide tube 15 by the distal-end needle portion 17a is prevented.

That is, the operator inserts the stylet 19 into the needle pipe 17, and the distal end portion of the stylet 19 is configured to be protruded from the distal-end needle portion 17a of the needle pipe 17. And the needle pipe 17 into which the stylet 19 is inserted is inserted into the insertion path 15a of the guide tube 15 from the proximal end of the handle 12. The distal ends of the needle pipe 17 and the stylet 19 are arranged in the vicinity of the taper portion 21 of the guide tube 15 as shown in FIG. 7B.

Next, the operator arranges the medical treatment device 11 configured by inserting the needle pipe 17 into which the stylet 19 is inserted into the guide tube 15 as mentioned above at the treatment instrument insertion port 60 of the ultrasonic endoscope 50 inserted into a body cavity and by which an organ in the body cavity is observed. At that time, first, the device is inserted into the treatment instrument insertion port 60 from the taper portion 21 side of the guide tube 15. Then, the guide tube 15 is inserted toward the distal end portion 53. The guide tube 15 of the medical treatment device 11 inserted into the treatment instrument insertion channel 55 of the insertion portion 52 reaches the distal end portion 53 of the insertion portion 52 in the ultrasonic endoscope 50 as shown in FIG. 7C. FIG. 7C shows schematic configuration of the distal end portion 53 of the insertion portion 52 in the ultrasonic endoscope 50. Reference numeral 54 denotes an ultrasonic transducer portion, in which an ultrasonic transducer for transmitting/receiving an ultrasonic signal is arranged.

That is, the operator carries out insertion operation to insert the guide tube 15 of the medical treatment device 11 configured by inserting the needle pipe 17 with the stylet 19 inserted therein into guide tube 15 into the treatment instrument insertion channel 55 of the ultrasonic endoscope 50.

It may be so configured that the operator inserts the guide tube 15 of the medical treatment device 11 into the treatment instrument insertion channel 55 of the ultrasonic endoscope 50 in advance before insertion into the body cavity so that the medical treatment device 11 inserts the integral ultrasonic endoscope 50 into the body cavity.

Figure 8A:
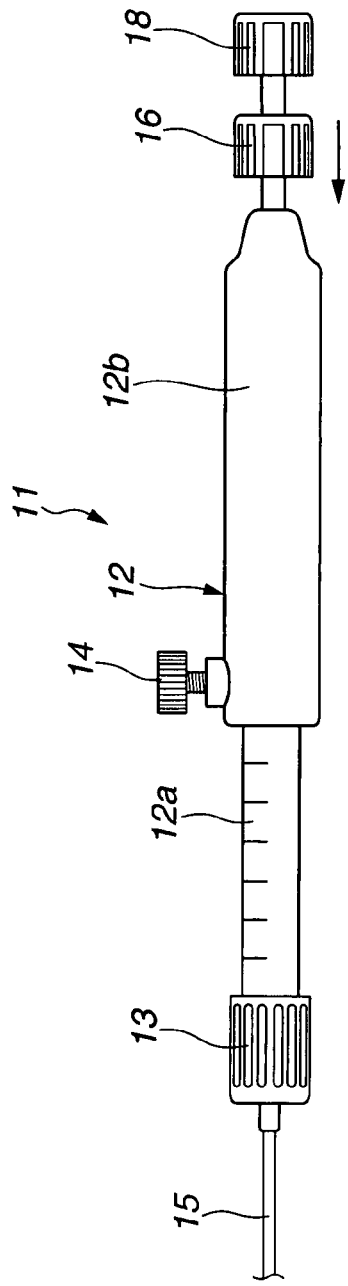
FIG. 8A is a view for explaining an operation to protrude the needle pipe into which the stylet is inserted from the guide tube.
Figure 8B:
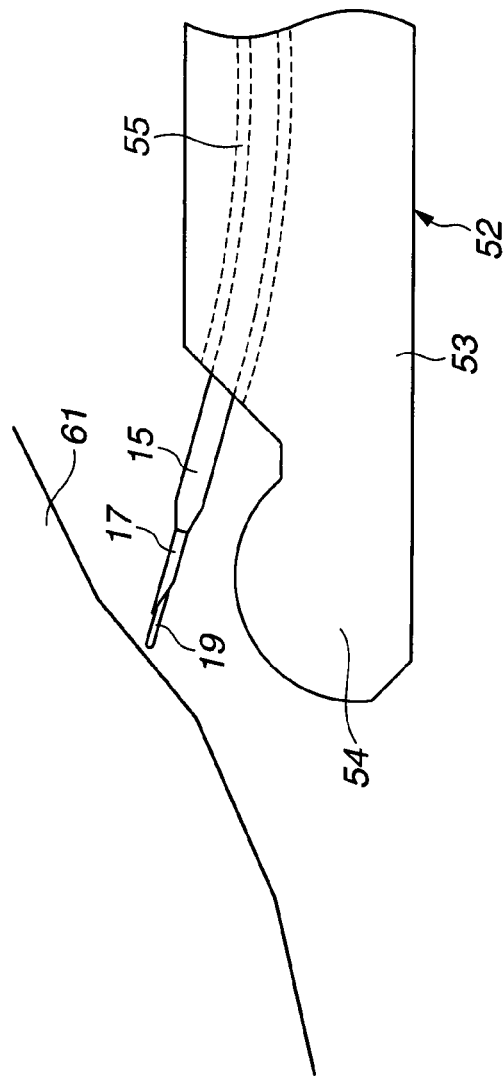
FIG. 8B is a state where the needle pipe into which the stylet protruded from the guide tube is inserted is led out toward a digestive tract wall.

FIG. 8A is a view for explaining an operation to protrude the needle pipe into which the stylet is inserted from the guide tube, and FIG. 8B is a view illustrating a state where the needle pipe into which the stylet protruded from the guide tube is inserted is led out toward a digestive tract wall.

Next, the operator protrudes the guide tube 15 of the medical treatment device 11 from the distal end portion 53 of the insertion portion 52 in the ultrasonic endoscope 50 inserted into the body cavity. At this time, the operator pushes out and operates the needle pipe base 16 and the stylet base 18 toward the handle 12 as shown by an arrow in FIG. 8A. Then, the needle pipe 17 into which the stylet 19 is inserted is led out toward the distal end from the distal-end opening 22 of the taper portion 21 in the guide tube 15. Moreover, the operator slides the slider portion 12b of the handle 12. Then, the guide tube 15 in the state where the needle pipe 17 into which the stylet 19 is inserted is let out toward the distal end is led out toward the digestive tract wall 61, which is a portion to be observed, as shown in FIG. 8B.

That is, the operator leads out the guide tube 15 of the medical treatment device 11 and the needle pipe 17 into which the stylet 19 led out of the guide tube 15 is inserted from the distal end portion 53 of the insertion portion 52 in the ultrasonic endoscope 50 toward the observation portion.

FIG. 9A is a view for explaining an operation to pull down the stylet protruding from the distal-end needle portion of the needle pipe, and FIG. 9B is a view illustrating a state where the distal-end needle portion of the needle pipe is opposed to the digestive tract wall.

Next, the operator opposes the needle pipe 17 of the medical treatment device 11 led out of the distal end portion 53 of the insertion portion 52 in the ultrasonic endoscope 50 to the digestive tract wall 61. After that, the operator pulls out and operates the stylet base 18 in a direction to be pulled out of the needle pipe base 16 as shown by an arrow in FIG. 9A. By this, the distal end of the stylet 19 is moved into the hollow portion at the hand side at least from the distal-end needle portion 17a of the needle pipe 17. Since the distal end of the stylet 19 is moved from the distal end needle portion 17a of the needle pipe 17, the needle pipe 17 and the guider tube 15 are stuck into the digestive tract wall 61 being observed by the ultrasonic endoscope 50 as shown in FIG. 9B.

That is, the operator leads out the distal end of the guide tube 15 constituting the medical treatment device 11 and the needle pipe 17 into which the stylet 19 is inserted and which is led out of the distal end of the guide tube 15 toward the observation portion. After that, an operation is performed so that the stylet 19 protruded from the distal end of the needle pipe 17 is moved and the distal-end needle portion 17a of the needle pipe 17 is opposed to the digestive tract wall 61.

Figure 10A:
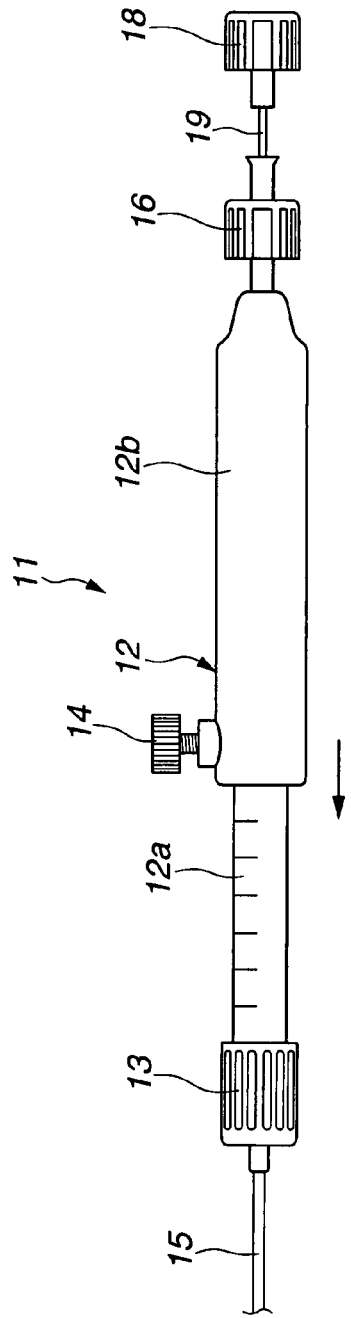
FIG. 10A is a view for explaining an operation to stick the needle pipe and the guide tube into a lesion.
Figure 10B:
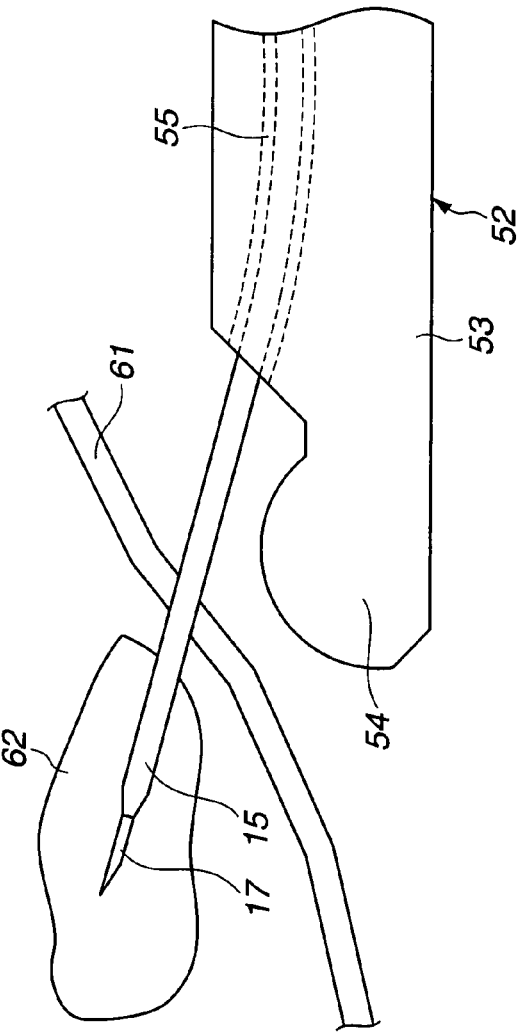
FIG. 10B is a view for illustrating a state where the needle pipe and the guide tube are stuck into the lesion.

FIG. 10A is a view for explaining an operation to stick the needle pipe and the guide tube into a lesion, and FIG. 10B is a view for illustrating a state where the needle pipe and the guide tube are stuck into the lesion.

Next, the operator slides the slider portion 12b of the medical treatment device 11 in which the stylet 19 has been moved from the distal-end needle portion 17a of the needle pipe 17 as shown by an arrow in FIG. 10A. Then, with the sliding of the slider portion 12b, the needle pipe 17 and the guide tube 15 are moved toward the digestive tract wall 61 being observed by the ultrasonic endoscope 50. And as shown in FIG. 10B, the needle pipe 17 protruded from the guide tube 15 is passed through the digestive tract wall 61 and stuck into the lesion 62 of the organ. At this time, with puncture of the needle pipe 17 into the lesion 62, the guide tube 15 is passed through the digestive tract wall 61 and stuck into the lesion 62.

That is because the distal end portion of the guide tube 15 has the taper portion 21 and the diameter 4B of the distal-end opening 22 and the outer diameter $\phi C$ of the needle pipe 17 are set at the substantially same dimension. By this arrangement, according to a puncture hole formed by the distal-end needle portion 17a of the needle pipe 17 from the digestive tract wall 61 to the lesion 62, the guide tube 15 is also easily stuck.

That is, the operator carries out a puncture operation to stick the guide tube 15 in which the needle pipe 17 constituting the medical treatment device 11 is protruded from the distal end with respect to the lesion 62 to be observed by the ultrasonic endoscope 50.

Figure 11A:
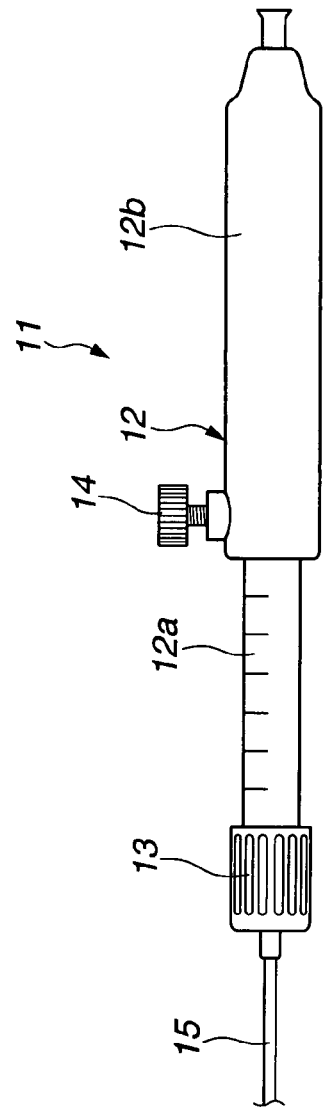
FIG. 11A is a view illustrating a state where the needle pipe is removed from the handle of the medical treatment device.
Figure 11B:
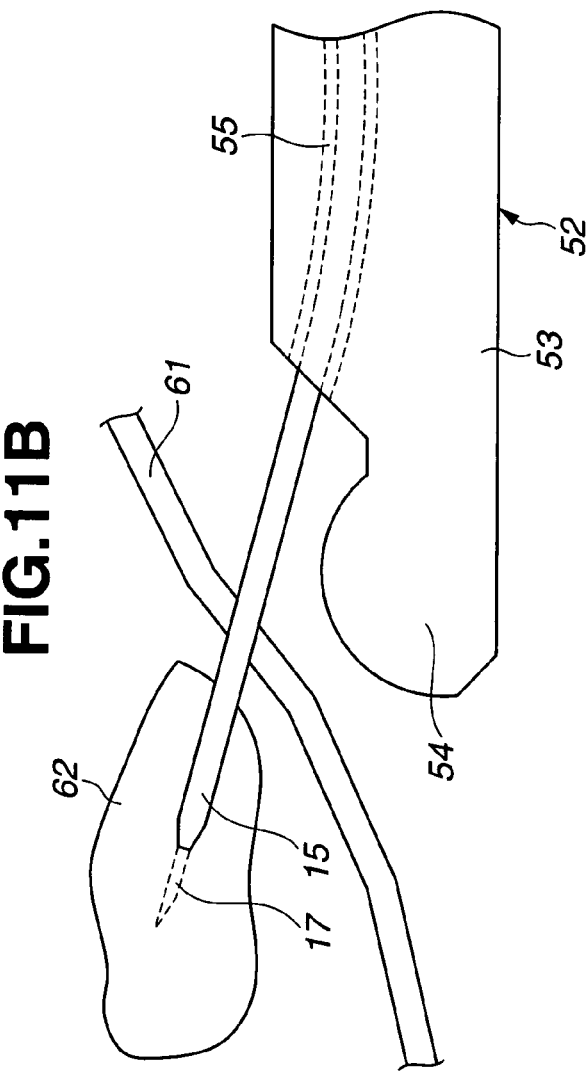
FIG. 11B is a view illustrating a state where the needle pipe has been removed and only the guide tube is stuck into the lesion.

FIG. 11A is a view illustrating a state where the needle pipe is removed from the handle of the medical treatment device, FIG. 11B is a view illustrating a state where the needle pipe has been removed and only the guide tube is penetrated into the lesion.

Next, the operator pulls the needle pipe base 16 from the handle 12 as shown in FIG. 11A in the medical treatment device 11 in which the needle pipe 17 and the guide tube 15 are stuck into the lesion 62 so as to pull out the needle pipe 17 from the guide tube 15. By this operation, the guide tube 15 from which the needle pipe 17 is pulled out as shown in FIG. 11B is brought into the stuck state into the lesion 62. When the needle pipe 17 is removed from the guide tube 15, the fixing screw 14 is tightened. By this, displacement of the slider portion 12 and the guide tube 15 is prevented.

That is, the operator carries out an operation to bring only the guide tube 15 stuck into the lesion 62 among the needle pipe 17 and the guide tube 15 having been stuck into the lesion 62 in the medical treatment device 11.

FIG. 12A is a view illustrating a configuration of the handle side of the medical treatment device whose treatment probe is inserted into the guide tube, FIG. 12B is a view illustrating a state where an electrode portion of the treatment probe is inserted and stuck into a lesion.

Next, in the medical treatment device 11 in the state where the guide tube 15 is stuck into the lesion 62, the operator arranges the treatment probe 31 into the guide tube 15 from the proximal end of the handle 12 as shown in FIG. 12A instead of the removed needle pipe 17. At that time, first, the electrode portion 34 provided at the distal end of the flexible pipe portion 33 is inserted into the guide tube 15 so as to insert the electrode portion 34 toward the lesion 64. Then, the electrode portion 34 provided at the treatment probe 31 inserted into the guide tube 15 is led out to the lesion 62 from the distal-end opening 22 of the guide tube 15.

The diameter 4B of the distal-end opening 22 provided at the guide tube 15 is set smaller than the outer diameter φD of the flexible pipe portion 33 of the treatment probe 31. However, since the slit 23 is provided at the taper portion 21, the distal-end opening 22 is pushed wide by the electrode portion 34 provided at the distal end of the flexible pipe portion 33. That is, the diameter of the distal-end opening 22 is expanded, and the electrode portion 34 of the treatment probe 31 is led out to the lesion 62. At the lesion 62, the puncture hole of the needle pipe 17 having been stuck once and then, removed remains. Therefore, the electrode portion 34 can be easily led out to the punctured position.

That is, the operator inserts the treatment probe 31 through the guide tube 15 in the stuck state into the lesion 62 of the medical treatment device 11. And the operator carries out an operation to arrange the electrode portion 34 provided at the treatment probe 31 at the lesion 62 where the needle pipe 17 has been stuck.

The medical treatment device 11 in which the treatment probe 31 is arranged supplies a radio-frequency current to the electrode portion 34 from the radio-frequency power supply device 38 after the electrode portion 34 of the treatment probe 31 is introduced into the lesion 62 through the guide tube 15 stuck into the lesion 62. Then, the lesion 62 is cauterized and treated by the radio-frequency current from the electrode portion 34 of the treatment probe 31 having been stuck. At this time, expansion of the cautery range to the living tissue other than the lesion 62 can be prevented.

Also, as mentioned above in FIGS. 4A and 4B, the length L of the needle pipe 17 and the length L of the flexible pipe portion 33 of the treatment probe 31 are set at the same dimension. By this arrangement, the electrode portion 34 located at the distal end of the flexible pipe portion 33 of the treatment probe 31 can be inserted to the position of the lesion 62 where the distal-end needle portion 17a of the needle pipe 17 is stuck. Moreover, with the same length L2 and the position of the electrode portion 34 provided with the first electrode 35a and the second electrode 35b of the treatment probe 31, the ultrasonic reflective machined surface 17b is provided at the distal-end needle portion 17a of the needle pipe 17 with the same length L2 and the position. By this arrangement, the operator can easily confirm the position of the distal end of the needle pipe 17 and the position of the electrode portion 34 of the treatment probe 31 by the ultrasonic image.

Figure 13A:
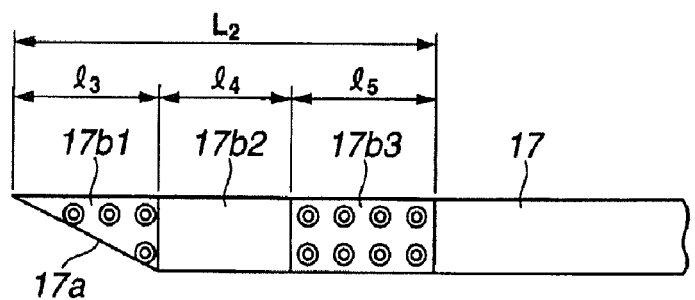
FIG. 13A shows an ultrasonic reflective surface at the distal end of the needle pipe.
Figure 13B:
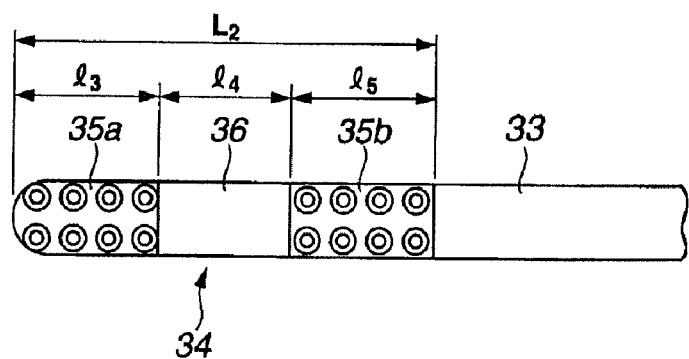
FIG. 13B shows the distal-end electrode portion of the treatment probe.

In order to clarify a position relation between the position of the distal-end needle portion 17a of the needle pipe 17 in the lesion 62 and the position of the electrode portion 34 of the treatment probe 31 using an ultrasonic image, the ultrasonic reflective surface may be configured as shown in FIGS. 13A, 13B.

Figure 13C:
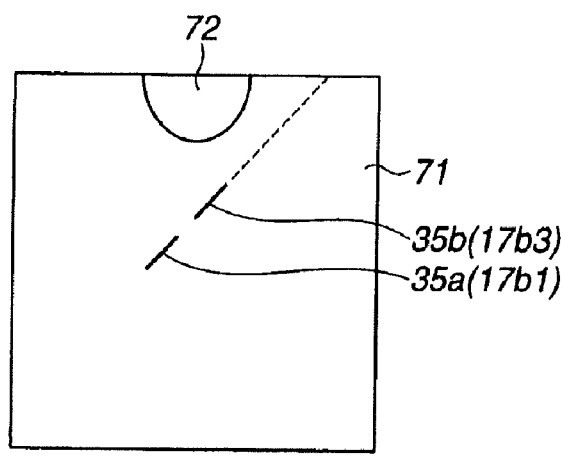
FIG. 13C is a display example of the treatment probe and the needle pipe displayed on an ultrasonic image.

FIG. 13A is a view for explaining an ultrasonic reflective surface provided at the distal end of the needle pipe, FIG. 13B is a view illustrating an ultrasonic reflective surface provided at the electrode portion of the treatment probe, and FIG. 13C is a view for explaining a state where the treatment probe having the ultrasonic reflective surface or the needle pipe is displayed on an ultrasonic image.

As shown in FIGS. 13A, 13B, the length of the first electrode 35a constituting the electrode portion 34 of the treatment probe 31 is set at 13, the length of the insulation portion 36 at 14, and the length of the second electrode portion 35b at 15. Then, at the needle pipe 17, a first reflection portion 17b1 with the length 13, a low reflection portion 17b2 with the length 14, and a second reflection portion 17b3 with the length 15 are also provided in the order from the distal end side. An ultrasonic reflectivity of the low reflection portion 17b2 is set lower than the ultrasonic reflectivity of the first reflection portion 17b1 and the second reflection portion 17b3.

Therefore, while the lesion is being observed as shown in an ultrasonic image 71 in FIG. 13C, the positions of the first reflection portion 17b1 and the second reflection portion 17b3 of the needle pipe 17 and the positions of the first electrode 35a and the second electrode 35b of the treatment probe 31 are displayed at substantially the same positions in the ultrasonic image 71. By this, the needle pipe 17 can be accurately stuck into the position to cauterize the lesion 62, and when the treatment probe 31 is inserted and stuck from the positions of the first reflection portion 17b1 and the second reflection portion 17b3 of the stuck needle pipe 17, the positions of the first electrode portion 35a and the second electrode portion 35b constituting the electrode portion 34 can be confirmed. Moreover, it becomes possible to assume a radio-frequency cautery range by the first electrode 35a and the second electrode 35b of the treatment probe 31 at the lesion 62 from the positions of the first reflection portion 17b1 and the second reflection portion 17b3 sandwiching the low reflection portion 17b2 between them. Reference numeral 72 in FIG. 13C indicates the position of the ultrasonic transducer.

In the description on the embodiments of the present invention, the ultrasonic reflection portions 35a1, 35a2, 35a3, 35b1, 35b2, and 35b3 provided at the first electrode 35a and the second electrode 35b constituting the electrode portion 34 of the treatment probe 31 are described to be formed on the surface of the first electrode 35a and the second electrode 35b, respectively. However, instead of formation on the surface, the ultrasonic reflection portions 35a1 to 35b3 may be formed on the inner circumferential face of the first electrode 35a and the second electrode 35b or a member with the ultrasonic reflection portions 35a1 to 35b3 provided may be attached on the inner circumferential face side of the first electrode 35a and the second electrode 35b.

As mentioned above, with the medical treatment device according to the embodiments of the present invention, the electrode portion of the treatment probe such as a bipolar radio-frequency cautery treatment instrument can be inserted and stuck into the lesion of an organ at the depth of the digestive tract wall in the body cavity for easy confirmation and cautery treatment of the lesion.

The present invention is not limited only to the above-mentioned embodiments but capable of various variations in a range not departing from the gist of the invention.

The invention claimed is:
1. A medical treatment device comprising:
an ultrasonic endoscope comprising an observation window, an illumination window, a treatment instrument opening and an ultrasonic transducer capable of transmitting and receiving an ultrasonic wave at a distal end portion of an insertion portion configured to be inserted into a body cavity, wherein a treatment instrument inser- tion channel is in communication with the treatment instrument opening provided in the insertion portion;

a guide tube inserted into the treatment instrument insertion channel of the ultrasonic endoscope and configured to be introduced into the body cavity;

a hollow needle pipe inserted into the guide tube;

a stylet, the stylet adapted to be inserted through the hollow needle pipe;

the hollow needle pipe, having an outer diameter, capable of being inserted into and removed from the guide tube, the hollow needle pipe capable of forming a puncture hole in a lesion;

a treatment probe having an electrode portion having an outer diameter larger than the outer diameter of the hollow needle pipe inserted into the guide tube, the treatment probe capable of being inserted into the puncture hole, the electrode portion including a first electrode and a second electrode insulated and separated from each other by an insulation portion for a radio-frequency cautery treatment for the lesion; and an ultrasonic reflection portion for reflecting an ultrasonic signal emitted from the ultrasonic transducer of the ultrasonic endoscope toward the ultrasonic transducer, the ultrasonic reflection portion being formed on surfaces of the first electrode and the second electrode of the treatment probe, wherein the hollow needle pipe comprises an ultrasonic reflective surface, the ultrasonic reflective surface having about the same length as a length of the electrode portion formed at the treatment probe and is arranged at a position corresponding to a position of the electrode portion, wherein the ultrasonic reflective surface of the hollow needle pipe comprises a first reflection portion, a second reflection portion and a low reflection portion, an ultrasonic reflectivity of which is lower than an ultrasonic reflectivity of the first reflection portion and an ultrasonic reflectivity of the second reflection portion, the low reflection portion is provided between the first reflection portion and the second reflection portion, and a length of the first reflection portion, a length of the low reflection portion and a length of the second reflection portion are set to be about the same as a length of the first electrode, a length of the insulation portion and a length of the second electrode of the electrode portion of the treatment probe, respectively, wherein the hollow needle pipe includes on the ultrasonic reflective surface thereof the ultrasonic portion for reflecting the ultrasonic signal emitted from the ultrasonic transducer of the ultrasonic endoscope toward the ultrasonic transducer, and wherein the ultrasonic reflection portion is a recess and projection portion or a rough-surfaced potion.

2. The medical treatment device according to claim 1, wherein a length from a distal-most end of a distal-end needle portion of the hollow needle pipe to a hollow needle pipe base is about the same as a length from a distal end of the first electrode to a base of a grasping portion.

3. The medical treatment device according to claim 1, wherein the recess and projection portion of the ultrasonic reflection portion is a sucker-state, V-shaped groove or rectangular groove.

* * * * *